(12) United States Patent
Kakonyi

(10) Patent No.: US 6,536,438 B1
(45) Date of Patent: Mar. 25, 2003

(54) CONDOMS WITH IMPROVED SECURITY

(76) Inventor: Arpad Kakonyi, Radnoti Miklos utca 13, H-6353 Dusnok (HU)

( * ) Notice: Subject to any disclaimer, the term of this patent is extended or adjusted under 35 U.S.C. 154(b) by 0 days.

(21) Appl. No.: 09/485,834

(22) PCT Filed: Aug. 19, 1998

(86) PCT No.: PCT/HU98/00079
§ 371 (c)(1),
(2), (4) Date: Apr. 6, 2000

(87) PCT Pub. No.: WO99/08630
PCT Pub. Date: Feb. 25, 1999

(30) Foreign Application Priority Data

Aug. 19, 1997 (HU) ................................ 9701417
Aug. 14, 1998 (HU) ................................ 9801885

(51) Int. Cl.⁷ .................................................. A61F 6/04
(52) U.S. Cl. ........................................ 128/844; 128/918
(58) Field of Search ............................. 128/842, 844, 128/918; 604/347–353

(56) References Cited

U.S. PATENT DOCUMENTS

| | | | |
|---|---|---|---|
| 4,840,188 A | * 6/1989 | Heidenfelder | 128/844 |
| 5,082,004 A | 1/1992 | Reddy | |
| 5,137,032 A | * 8/1992 | Harmon | 128/844 |
| 5,333,621 A | * 8/1994 | Denzer | 128/844 |
| 5,626,149 A | 5/1997 | Schwartz | |
| 5,806,524 A | * 9/1998 | Hernandez | 128/844 |

FOREIGN PATENT DOCUMENTS

| GB | 2181953 | 5/1987 |
|---|---|---|
| GB | 2229922 | 10/1990 |

* cited by examiner

Primary Examiner—Michael A. Brown
(74) Attorney, Agent, or Firm—Ladas & Parry

(57) ABSTRACT

The invention relates to condoms with improved security having an oblong container open at one end and having an adhesive layer applied in a ring form on the inner surface of its open end. The novel condoms cover the penis essentially in its full length and the adhesive layer is situated in the area closer to the open end of the condom, preferably on the first third thereof. The condoms remain firmly on their place during coitus and active ingredients can also be contained within them to achieve desired effects, e.g. to prevent precocious ejaculation.

2 Claims, 2 Drawing Sheets

CONDOMS WITH IMPROVED SECURITY

TECHNICAL FIELD OF INVENTION

The invention relates to condoms with improved security.

BACKGROUND ART

Nowadays condoms are the most wide-spread and from many aspects the most secure contraceptive devices which protect also against STD-s (sexually transmitted diseases). Nevertheless many people feel repugnance to condoms since the fear from slipping down thereof causes psychic troubles.

To solve the problem of slipping down a size choice of the condoms recently available commercially has been offered. When choosing the condom size users take into consideration the sizes of penis in full erection. During coitus, however, erection can decrease in such an extent mainly due to postponement of ejaculation which decrease can not be followed properly by the condom. Consequently the generally used condoms stay at the desired position only in the erected state of a penis.

Although anatomical appearance of the penis may be very different individually, the blood leaves at first from the front part thereof i.e. from the glans penis when erection decreases. Then the penis will take a tapering conical form so the condom can slip down easily. Some manufacturers sell so-called comfortable varieties of condoms which have an increased diameter at their closed end. Also this variety is advantageous in full erection only, moreover, by an anatomical appearance showing a glans penis with a diameter less than that of the diameter of the body of the penis it is decidedly disadvantageous as the condom can slip down more easily.

A wide scale of spermicides and lubricants is used on up-to-date condoms, The outstanding effects exerted by such substances are required by the users, however, should the erection decrease such materials promote slipping down of the condom.

In a state of decreased erection the vaginal discharge can also get into the inner part of the condom and the lubricating effect of this discharge might also promote slipping down of the condom.

Sperms can get out of the penis also before ejaculation in the presemen. During a decreased erection these sperms can get out of the slipped down condom similarly to the sperms ejaculated. The seminal fluid itself also has a lubricating effect.

A further problem is that in case if the condom slips down during a decreased erection then the pathogens of STD-s can cause an infection either by getting into the inner part of the condom or by getting out of it.

Due to the decreasing erection the coitus has to be terminated immediately after ejaculation so that the condom can not stay in the vagina and its content can not be emptied thereto.

A frequent cause for tearing the condoms is that they are hurt by the nails of users trying to retain them on their place when they are felt slipping down. Once the slipping down of the condom could be hindered there would be no need to retain it by the hand and therefore the danger of its tearing would be diminished.

The above problems separately or altogether lead to the psychic troubles connected with the condom use which problems are the main causes for the repugnance from the condom use and which finally can cause also an urging of ejaculation impairing thereby the quality of coitus. As the use of the condoms now commercially available requires an intensive attention it is hard to achieve an undisturbed coitus by their use.

Hungarian Patent No. 162 959 describes a contraceptive condom that can be stuck to the penis. The condom disclosed therein has an adherent layer applied in a ring form on the inner surface of its open end having a rim which rim is suitably perforated. A removable protecting cover is stuck over the adherent layer and a handling cover made of a more stiff material is stuck removably to the outer surface of the container in order to protect the material of the container and to enable users to take the condom thereby while sticking it.

The condom disclosed in the above Hungarian patent specification is in fact a little sacculus that can be put to the tip of the penis; it has a really small size and its primary purpose beside hindering the sperms in getting out of the condom is to cover as a small part from the surface of the penis as possible and thereby to diminish the decrease of the direct contact between the partners due to the condom use in the slightest degree possible (column 4, paragraph 4). In case of the condoms used formerly and made of relatively thick rubber this solution could improve the quality of coitus with condom use by letting the more sensible parts of the penis uncovered. In case of the nowadays wide-spread condoms made of very thin rubber, however, this advantage shrinks into insignificance beside the disadvantage that the disclosed condom covering only the tip of the penis provides no protection against the STD-s. AIDS and other STD infections can be transmitted namely not only through the urethra but also through the small injuries occurring during coitus on the sensible parts of the penis which parts are uncovered by the condom disclosed in the Hungarian patent specification No. 162 959. The discharge getting into the condom through the holes of the perforated rim might also decrease the adhesive efficiency of the adhesive material.

A further disadvantage rendering also the practical applicability of the condom disclosed in Hungarian patent specification No. 162 959 questionable is that due to the small size of the condom and its localisation on the tip of the penis the adhesive material to be used on the inner surface at the open end of the condom on the sensible skin of the penis should possess such a strong effect which would irritate the skin considerably. Similarly, the solvent-containing cream or the liquid proposed for the removal of the condom (column 2, paragraph 2) might also cause a skin irritation and drying out of the skin since it has to be applied to a very sensitive skin surface. Neither the other possibility proposed for the afteruse removal of the condom, i.e. the mechanical removal can be imagined to be painless provided that the applied adhesive material is strong enough to keep the small size condom on its place during all the movements in the course of coitus.

A further problem is that the condom disclosed in Hungarian patent specification No. 162 959 is not adapted to the individual differences occurring in the skin of penis. The disc-shaped flat rim should fit to the skin plicae at the outlet part of urethra which renders the slip-proof, safe and comfortable applicability questionable also from anatomical point of view.

Hence up to now no condom is available which would surround the penis safely and in a slip-proof manner during the whole coitus, hinder discharges and pathogens in getting out of the condom or in getting into it by a perfect closing and thus protect against both unwanted pregnancy and infections.

The objective of the invention is to develop a condom with improved safety which does not slip down during coitus and thereby eliminates the above problems. The further objective of the invention is to develop a condom with improved safety which is suitable for achieving also additional desired effects, especially which is an aid in preventing precocious ejaculation (ejaculatio praecox).

DISCLOSURE OF THE INVENTION

The invention relates to a condom with improved safety fulfilling the above requirements, said condom having an oblong container open at one end and having an adhesive layer applied in a ring form on the inner surface of its open end; said condom is characterized in that it covers the penis essentially in its full length and the adhesive layer is situated on the first third of the open end of the condom.

Further the invention relates to a condom with improved safety fulfilling the above requirements, said condom having an oblong container open at one end and having an adhesive layer applied in a ring form on the inner surface of its open end; said condom is characterized in that it covers the penis essentially in its full length and the adhesive layer is situated in the area closer to the open end of the condom.

Condoms according to the invention surround an overwhelming part of the penis and the adhesive material applied in a ring form on the inner part of the condom either on the first third of the open end thereof or in the area closer to the open end thereof provides a perfect closing.

The adhesive material is applied in a circular ring form on the inner surface of the condom. It must by all means be applied farther back than the position of the drawn back foreskin because of the sensitivity of the foreskin, i.e. it has to adhere to the outer skin surface of the penis.

In the specification "ring form" is meant to cover all kinds of circular adhesive material applications which provide a perfect closing. The adhesive material applied in a ring form can be positioned e.g. as one or more circular, straight or wavy or zigzag stripe(s) or as any other similar shape providing a perfect closing.

The applied adhesive material is non-irritating for the skin, non-toxic and preferably environment-friendly. Either synthetic or natural adhesive materials can be applied, preferably adhesive materials generally applied in surgical plasters are used.

A great number of suitable adhesive materials is known and used in the transdermal medicine in the adhesive layers of plasters. Such adhesive materials are compatible with the skin and they are non-toxic. Examples of preferably applicable adhesive materials are listed hereinbelow without the intent of limitation:

polystyrene copolymers, e.g. Kraton® (Shell),
ethylene—vinylacetate derivatives, e.a. Elvax® (DuPont), Vynathene (U.S.J. Chemicals),
polybutadienes, e.g. Indopol® (Amoco),
polyisobutylenes, e.g. Oppanol® (BASF),
acrylic or metacrylic polymers, e.g. Acronal® (BASF).

Although the main components of the listed adhesive materials are the above basic polymers but the adhesive materials may have different compositions.

For reducing the individual sensitivity the adhesive material can contain also antiinflammatory materials capable of being absorbed through the skin and thus preventing inflammation thereof. Such antiinflammatory materials are for example hydrocortisone, hydrocortisone acetate, prednisolone, methyl prednisolone, triamcinolone acetonide, fludrocortisone, flurandrenolone, flumetazone, dexamethasone sodium phosphate, betamethasone valerate, fluocinolone acetonide, fluorometholone, pramoxine hydrochloride etc.

A person skilled in the art of transdermal medicinal technique can choose without difficulty the type and dose of the antiinflammatory material that can be admixed to a certain adhesive and can choose also one or more additive(s) promoting absorption.

Hence any adhesive material is suitable for forming the adhesive layer of the condom according to the invention provided that it is no-toxic, not irritating for the skin and does not interact with the material of the condom and/or with the applied antiinflammatory, spermicidal, lubricating or other materials that are present.

The adhesive material applied on the condom according to the invention does not interfere with the application of spermicidal and lubricating materials either on the outer or on the inner surface of the condom. In the condom manufacturing process after winding up of the part of the condom supplied with the adhesive layer spermicides and/or lubricants can be applied to the non-adherent condom parts.

In a preferred embodiment the adhesive material adheres both to the skin and to the rubber of the condom. In this case a non-adherent layer is applied on the outer surface of the condom positioned opposite to the adhesive layer in wound up state which non-adherent layer hinders adhering of the adhesive layer to the outer surface of the condom during winding up in the manufacturing process. The non-adherent layer can be formed in a per se known way, preferably e.g. by applying a thin plastic coating which is non-adherent to the particles of the used adhesive.

Another preferred way of forming a non-adherent layer is forming of a silicone layer. Silicone (polyorganosiloxane) has a well-known form-releasing, antiadherent capability.

In a further preferred embodiment the non-adherent layer positioned opposite to the adhesive layer has a width bigger than that of the adhesive layer.

In case of embodiments comprising an adhesive material that adheres well to the skin but does not adhere to the material of the condom, e.g. to simple rubber, that part of the inner surface of the condom which will bear the adhesive layer has to be rendered suitable for the application of the adhesive material by a pre-treatment. In such a case there is no need of forming a non-adherent layer positioned opposite to the adhesive layer on the outer surface.

A further preferred embodiment comprises two or more layers in the adhesive layer applied on the condom. The layer facing the condom has to contain an adhesive material having good adherence to the rubber or the adhesive material in that layer has to be applied on an area of the inner condom surface that had been pre-treated to improve adherence, while the layer facing the skin has to contain an adhesive material having good adherence to the skin.

A further objective of the invention is to provide a condom with improved safety which fulfils the above-listed requirements and in addition thereto makes it possible to introduce certain active ingredients directly into the skin and thereby to aid achieving further desired effects.

Such a desired effect is to prevent precocious ejaculation. In such a case spreading of local anaesthetic solutions or ointments over the clans penis and the foreskin is proposed. However, this leads to disadvantageous effects for omen since the uncontrollable amount of topical anaesthetics getting into the female genital organs from the penis during the coitus hinders reaching of the female orgasm.

It has been found that this problem can be solved by an embodiment of the condom with improved safety according to our invention by putting the local anaesthetic suitably within the condom, together with antiinflammatory materials if necessary.

As a local anaesthetic numerous known local anaesthetic materials can be used in the practice of local anaesthesia the most wide-spread substance is lidocaine (Xylocaine). The reasons for this are its good elimination ability (2,2 mg/kg/minute), its minimal toxicity and in addition thereto its good sensory nerve terminal paralysing effect.

Instead of lidocaine other known topical anaesthetics can also be used, some examples of which are listed hereinbelow without the intent of limitation: procaine, lidocaine hydrochloride, amethone, hostacaine, cyclomethycaine, dyclonine, hexylcaine, hydroxyprocaine, hydroxytetracaine, leucinocaine, mepivacaine, bupivacaine, marcaine, pramocaine, quinisocaine, norcaine, etc.

10 ml active ingredient containing a topical anaesthetic can be prepared e.g. (but not exclusively) in the following manner.

The components listed hereinbelow:
1 g lidocaine/Xylocaine, 2-(diethylamino)-N-(2,6-dimethylphenyl)acetamide/;
preferably 60–70% by volume Polyoxaethanum-400 polyoxyethylene, polyethyleneglycol, molecule size n=about 8;
preferably 30–40% by volume Polyoxaethanum 1540 polyoxyethylene, molecule size n=33–35; are admixed in a mixing vessel (equipment).

The antiinflammatory material used together with the local anaesthetic if necessary may be for example (but not exclusively) any of the antiinflammatory materials listed above as compatible with the adhesive material.

A person having ordinary skill in the art can choose the type and the amount of carriers and/or auxiliaries as well as the necessary dose for a given local anaesthetic. It should be taken into account as a hindering reason that the components of the mixture containing the active ingredient must not interact with the spermicide eventually wished to be used simultaneously.

Moreover, it has been found that within the condom according to the invention e.g. stimulants, materials increasing hyperaemia can also be contained, which stimulants can be used also together with antiinflammatory materials, further other active ingredients or active ingredient combinations can also be contained. Beside the component exerting the desired effect the used active ingredients can contain also proper auxiliaries aiding penetration into the skin and exertion of the effect.

Hence another preferred embodiment of the condom according to the invention with active ingredient contains stimulants, materials increasing hyperaemia instead of the local anaesthetic exerting an effect contrary to the effect of stimulants. Since stimulants rubbed into the skin of the penis can dissolve into the female genital organs during coitus and can cause undesired effects there, it can be reasonable to place also such materials within the condom. The applicable known stimulants, materials increasing hyperaemia can be e.g., but not exclusively the following ones: capsaicin (stimulating the thermosensitive nerve terminals, causes a burning, warm feeling and hyperaemia), camphor, potash soap, soda soap, allyl isothiocyanate, mustard oil, aetheroleum terebinthinae rectificatum, nicotinic acid benzylester, pyridine β-carboxylic acid benzylester, nicotinic acid β-buthoxyethylester, nicotinic acid tetrahydrofurfurylester, etc. Some of the listed substances may cause inflammation therefore they are reasonably used simultaneously with a known antiinflammatory material. A person having ordinary skill in the art can select the dose to be used and the quantity of the auxiliaries also in connection with these substances.

The most preferred embodiments of the invention are illustrated on the figures explained in details hereinbelow, however, the scope of the invention is not limited to the embodiments shown on these figures.

Figure 1:
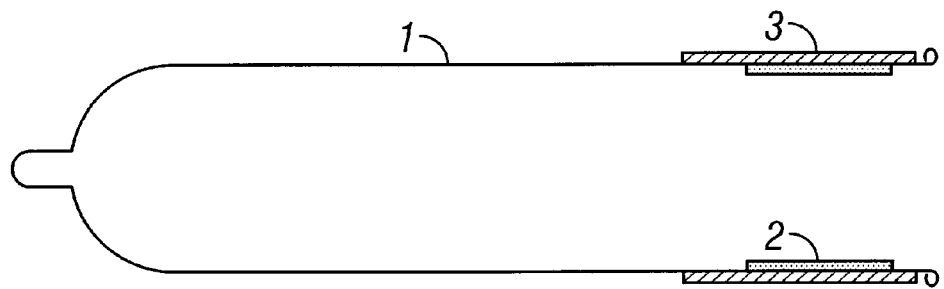
FIG. 1 shows an embodiment of the condom according to the invention wherein a non-adherent layer is positioned opposite to the adhesive layer.

The preferred embodiment of the condom shown on FIG. 1 has an open container 1, an adhesive layer 2, and a non-adherent surface 3. The embodiment shown on FIG. 1 has an adhesive layer 2 applied as a straight stripe having a width of 25 mm. The non-adherent surface 3 is slightly shifted compared to the stripe of the adhesive layer 2, i.e. the former is wider than the latter in order to achieve that by winding up the adhesive layer 2 be positioned opposite to non-adherent surface 3. Of course it is possible to apply the adhesive layer 2 instead of a stripe in the form of more than one straight, wavy, zigzag or otherwise shaped stripes forming closed lines. The preferred width of the adhesive layer is 20–30 mm at this embodiment.

Figure 2:
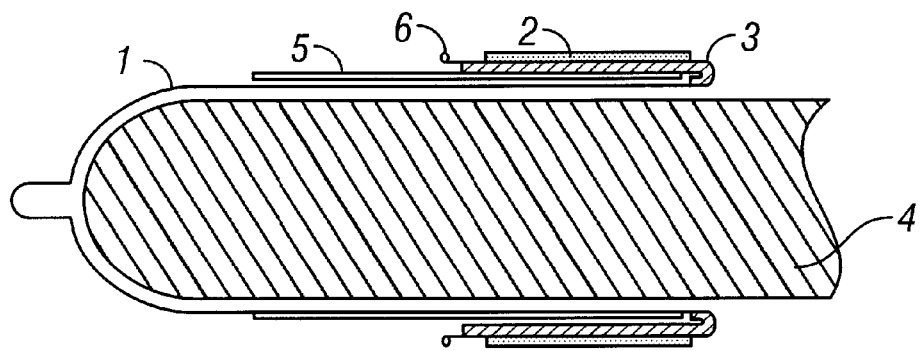
FIG. 2 illustrates one step of a possible manufacturing technology suitable for manufacturing the condom according to the invention.

FIG. 2 illustrates one step of a possible manufacturing technology suitable for manufacturing the condom according to the invention.

One possible realisation of the manufacturing process is described hereinbelow as an illustration. A condom-shaped open container 1 made of latex starting material is prepared in a conventional manner then it is drawn to a silicone rubber cylinder 4 fitting to its size. At the open end of the open container 1 the outer surface is made non-adherent in a circular stripe having a width of 5 cm by applying a silicone layer 2 starting at a distance of 1.5 cm from the open end. Then a silicone rubber tube 5 having a wall thickness of 2 mm is pushed onto the open container 1 from the direction of the closed end thereof and an about 5 cm long turned out part of the open end of the open container 1 is pulled thereon. An adhesive layer having a width of 2 cm is applied by a known process (rolling) in a layer thickness corresponding to an amount of 3.5 mg/cm$^2$ in a circular form onto the surface starting at a distance of 2.5 cm from the thicker ring 6 positioned at the open end of the open container 1. Acronal® 102 L (BASF) is used as an adhesive material which is polyacrylic acid ester based copolymer dissolved in benzine and having the following characteristics: thermally curable (optimally 90 sec/100° C.); viscosity at 23° C. is 600–1900 mPa/sec (DIN 53019); flash point is −34° C. (DIN 51755); density is 0.77 g/cm$^3$ at 20° C.

The adhesive material is cured by blowing of air having a temperature of 100° C. for 90 seconds. Then the adherent surface is turned back to the silicone rubber cylinder 4 by pushing forward the silicone rubber tube 5. Thereafter the condom can be wound up in a conventional manner without the adhesive material being adhered to the cylinder.

Figure 3:
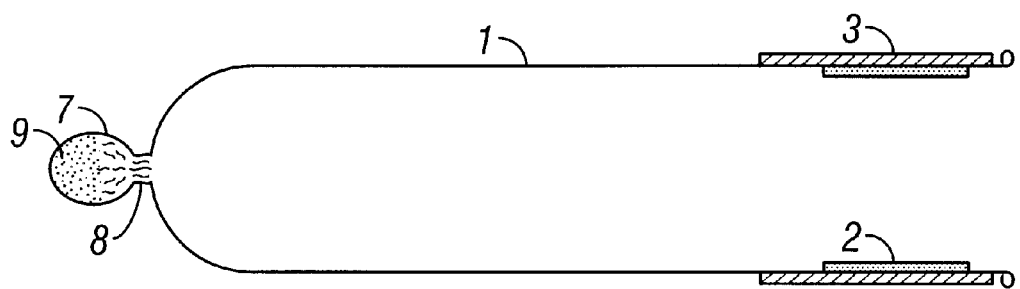
FIG. 3 shows an embodiment of the condom according to the invention wherein active ingredient is contained in the sperm collecting sacculus.

FIG. 3 is a further preferred embodiment of the condom according to the invention. One possible application area for this embodiment is the prevention of precocious ejaculation. By this embodiment the active ingredient (in case of a condom for the prevention of precocious ejaculation the local anaesthetic) or the mixture containing the active ingredient is contained within the condom, preferably in the sperm collecting sacculus 7 at the closed end of the condom; a sperm collecting sacculus of this type is generally present at the closed end of the conventional condoms, too. The adhesive layer 2 hinders getting out of the active ingredient from the condom during use. At the end of the sperm collecting sacculus 7 open to the inside part of the condom a narrowing 8 is formed (preferably by puckering of the material during manufacture) to keep the active ingredient 9/in the specification under the term "active ingredient" mixtures comprising one or more active ingredient(s) 9 or mixtures containing one or more active ingredient(s) 9 as their component(s) are also meant/within the sperm collecting sacculus 7 till the condom use. The volume of the sperm collecting sacculus after puckering is preferably at least 1 ml.

Auxiliaries can also be used admixed to the active ingredient contained within the condom. Such auxiliaries can be e.g. (but not exclusively) agents promoting absorption, antiinflammatory substances, conserving agents, stabilizers, etc.

When putting on a conventional condom the sperm collecting sacculus 7 should be compressed to expel air therefrom in order to enable said sacculus to hold the sperm. When putting on the condom according to the invention the active ingredient 9 can be pushed out with the same move from the sperm collecting sacculus 7 onto the skin of the glans penis and it can be rubbed with a circular move on the full surface of the glans penis including also the frenulum. Thereafter the sperm collecting sacculus 7 fulfils its function normally as the narrowing 8 is able to widen.

Lower doses of the stimulant put within the condom as active ingredient can be contained in the sperm collecting sacculus 7 provided that they do not irritate more sensible areas of the penis in an undesired extent.

Active ingredients 9 having a more intensive effect can be incorporated also into the adhesive layer 2 adhering to the outer skin surface of the penis by a known process. Said process is the transdermal technique wide-spread in the medicine which may involve constructing one-layered or more-layered matrices adapted to the intended application by using adherent materials, active ingredients, chemical membranes promoting or controlling absorption and other auxiliaries in order to achieve a uniform controlled administration by protracting the release of active ingredients.

The active ingredients incorporated into the adhesive layer of the condom according to the invention serve for reaching quite a contrary purpose. In the course of the coitus the maximum quantity of active ingredient has to be introduced into the skin during the shortest time possible. In the most advantageous solution for this purpose the active ingredient is brought in direct contact with the skin, the auxiliaries applied serve for a quick absorption, adhesion of the active ingredient to the material of the condom is ensured by an intermediate adherent layer and the material density is adjusted so that the active ingredient remains on its place even at the winding down of the condom when putting it on. The increasing effect of the auxiliaries to the speed of absorption through the skin, the effective concentration and the friction movements during the coitus together lead to an abrupt active ingredient release.

During the manufacture of an embodiment containing active ingredient in its adhesive layer the process described above in connection with FIG. 2 can be followed till that step when a turned out part (which is preferably 8 cm long) of the open end of the condom is pulled onto the silicone rubber tube. In this case the silicone-covered stripe of the outer surface is wider, too, preferably it has a width of 9 cm.

An adherent layer serving as an intermediate adherent layer having a width of 5 cm and the smallest layer thickness possible is formed in a circular shape on the surface starting at 1.5 cm from the open end of the condom.

Thereafter the adhesive surface adhering to the skin is formed by applying a further adhesive layer so that a continuous adhesive stripe having a width of 5–8 mm is present at that edge of the adherent stripe which is positioned at the open end of the condom in order to hinder the active ingredient in getting out of the condom, and longitudinal stripes or spots ensuring also the adherence to the skin are formed on the remaining surface of the adherent layer. The active ingredient can be applied to the surface not covered by the second layer of the adhesive material.

If desired the whole system can be covered by a chemical membrane hindering the active ingredient in getting out of the condom before use, however, ensuring a quick penetration of the active ingredient through the membrane upon contacting the skin.

In case of a condom having a diameter of 32 mm the surface contacting the skin is 30–40 $cm^2$, provided that the surface adhering to the skin amounts to 20–40% of the whole surface. In case if the active ingredient can interact the spermicide eventually wished to be used then a continuous adhesive layer has to be formed also on that side of the adherent stripe which faces the inner part of the condom.

For a person having ordinary skill in-the manufacture of transdermal plasters the use of the transdermal technique in forming the active ingredient releasing adherent layer according to the invention does not create any problem.

An increase during the coitus in the layer thickness of the system applied at the open end of the condom is not disturbing even if the system would be swollen due to water absorption.

Figure 4A:
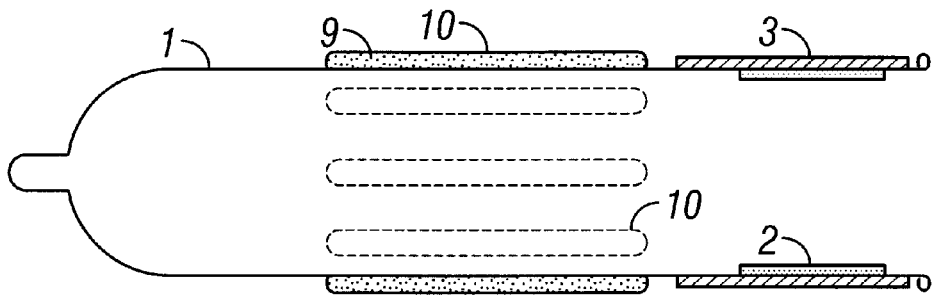
FIG. 4 illustrates an embodiment of the condom according to the invention wherein longitudinal containers serving for storing the active ingredient are formed on the inner surface of the condom.
Figure 4B:
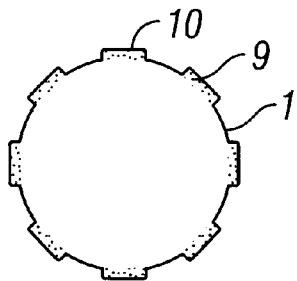

FIG. 4 shows another possible application of the active ingredient within the condom. On the starting material of the condom (which may be e.g. latex) containers 10 having preferably a longitudinal position and formed from the material of the condom are present on the area stretching from the adhesive layer 2 applied at the open end and from the non-adherent surface 3 positioned opposite thereto towards the closed end (preferably starting at a distance of 6 cm from the open end of the condom). The containers are present in form of recesses on the inner side and in form of bulges on the outer side. The containers 10 hold the active ingredient 9 preferably in such a manner that a chemical membrane not shown on the FIG. 4 hinders the active ingredient in getting out of the containers 10 before use. Permeability of the membrane applied if necessary, the carriers and auxiliaries applied if necessary, the optimal active ingredient dose and the friction movements promote introduction of the proper amount of active ingredient into the skin.

In so far as active ingredient 9 is contained within the condom according to the invention it can be contained in the sperm collecting sacculus and/or in the containers 10 formed from the material of the condom and separated by membranes if desired and/or in the adhesive layer.

The adhesive layer applied on the condom according to the invention ensures retaining of the active ingredient within the condom during use in case of all embodiments.

The advantages of the condom according to the invention are summarized as follows: the shaping of the condom hinders slipping down of the condom during the coitus, getting out of the sperms of the presemen from the condom, dripping out of the seminal fluid from the condom after ejaculation should the man not terminate the coitus immediately, getting into the condom or getting out of the condom of pathogen microorganisms, getting into the condom of vaginal discharges.

Further the possibility of tearing of the condom is also diminished since there is no need to keep the condom in its place by hand.

Thereby the condom provides a more secure feeling for the user, less attention is required during its use and the psychic troubles are decreased.

The condom according to the invention is manufactured in a known, usual way except for the application of an adhesive layer, further apart from the following steps if desired: forming the containers present on the inner surface of the condom, putting membranes to the inner surface of the condom and forming a non-adherent surface. The solution according to the invention can be used in case of all known condom forms covering an overwhelming part of the penis.

What is claimed is:

1. A condom with improved security having an oblong container of uniform diameter throughout, said container being open at one end and having an adhesive layer applied in a ring form on the inner surface adjacent its open end, wherein the condom covers the penis essentially in the full length thereof and said adhesive layer, having a width of 2–5 cm, is situated on the container about the first fourth thereof adjacent the open end, and said adhesive layer contains an adhesive material having a poor adherence to rubber and a good adherence to skin or good adherence both to rubber and skin, and wherein the adhesive layer is applied in an area of the inner wall of the condom that had been pretreated for a better adherence, and said adhesive layer has a circular ring adhesive layer form, a further adhesive layer applied in a direction towards the closed end of the condom in the form of longitudinal straight stripes or spots is present, and the adhesive layer consists of more than one layer from which the layer facing the condom contains an adhesive material having good adherence to rubber while the layer facing the skin contains an adhesive material having a good adherence to skin, a non-adherent outer surface of the condom, essentially opposite of the adhesive layer and said non-adherent surface of the condom has a width bigger than that of the adhesive layer, and an active ingredient, a stimulant, a local anesthetic, or an anti-inflammatory material are contained within the condom in a sperm collecting sacculus separated by a narrowing at the closed end of the condom and in containers having a longitudinal shape and formed from the material of the condom and separated by inner membranes or in the adhesive layer.

2. The condom of claim 1 wherein an inner membrane is fixed to the adhesive layer applied in the form of longitudinal stripes or spots on the inner wall of the condom, and wherein an active ingredient is contained in a space defined between the wall of the condom and said inner membrane.

* * * * *